United States Patent [19]
Osborne et al.

[11] Patent Number: 6,020,148
[45] Date of Patent: *Feb. 1, 2000

[54] IN VITRO METHOD FOR EYE AND SKIN IRRITATION TESTING

[75] Inventors: Rosemarie Osborne, Oxford; Mary Ann Perkins, Cincinnati; Deirdre Anne Roberts, Loveland, all of Ohio

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/877,963

[22] Filed: Jun. 18, 1997

Related U.S. Application Data

[63] Continuation of application No. 08/378,897, Jan. 26, 1995, abandoned, which is a continuation of application No. 08/115,901, Sep. 1, 1993, abandoned, which is a continuation of application No. 07/830,594, Feb. 19, 1992, abandoned.

[51] Int. Cl.[7] .................................................. C12Q 1/32
[52] U.S. Cl. ............................................. 435/26; 436/63
[58] Field of Search ........................... 435/26, 240, 241; 436/5, 63

[56] References Cited

U.S. PATENT DOCUMENTS

| | | | |
|---|---|---|---|
| 3,765,404 | 10/1973 | Turek | 128/2 |
| 3,926,723 | 12/1975 | Green et al. | 195/1.8 |
| 4,016,036 | 4/1977 | Green et al. | 195/1.8 |
| 4,533,635 | 8/1985 | Guédon born Saglier | 435/240 |
| 4,760,020 | 7/1988 | Neufeld | 435/29 |
| 4,835,102 | 5/1989 | Bell et al. | 435/29 |
| 4,963,489 | 10/1990 | Naughton et al. | 435/240.1 |
| 5,053,340 | 10/1991 | Bergman | 436/5 |

FOREIGN PATENT DOCUMENTS

| | | |
|---|---|---|
| 37 37 652 | 7/1989 | Germany . |
| 3737652 | 7/1989 | Germany . |
| WO 80/01350 | 7/1980 | WIPO . |

OTHER PUBLICATIONS

Steinberg M., A Comparison of Test Techniques Based on Rabbit and Human Responses to Irritants with Recommendations, Regrading the Evaluation of Mildly or Moderately Irritating Compounds, In Animal Models in Dermatology, H. Maibach ed., Churchill Livingst, 1975.

Anon, Research Dissertation Abstract 278,061, 1987.

Csato, et al., Intl. J. of Derm. 28 (2), 86–89 (Mar. 1989).

Gibson et al., Fd. Chem. Toxic., 21 (5) 587–94 (1983).

Rowan et al., Ann Rev. Pharmacol. Toxic., 25, 225–47 (1985).

Mosman, J. Immunological Methods, 65, 55–63 (1983).

Whitfield, et al., Exp. Cell Research, 35, 207–210 (1964).

Nixon et al. Regulatory Toxicology and Pharmacology, 12, 127–136 (Oct. 1990).

UpJohn, Immunology, The UpJohn Co, Kalamazaoo, MI 1991, p. 159.

Triglia, D, Cytotoxicity Testing Using Neutral Red . . . Toxic. In Vitro, vol. 5, No. 5/6 pp. 573–578. Received by us Subscribers Dec. 10, 1991.

Lawrence R., The Chorioallantoic Membrane In The Prediction Of Eye Irritation Potential Toxic In Vitro 4 (4/5) pp. 321–323 1990.

Osbourne R., In Vitro Skin Irritation Testing With Human Skin Cell Cultures, Toxic In Vitro 5(5/6) pp. 563–567 1991.

Yasuda, H., Ultrathin Coating by Plasma Polymerization Applied to Corneal Contact Lens, J Biomed Mater Res 9 629–643, 1975.

LabFax, Cell Culture Published by Bios Scientific Publishers, Edited by Butler, pp. 29–30, 1992.

*Primary Examiner*—Ralph Gitomer
*Attorney, Agent, or Firm*—Rose Ann Dabek; Bart S. Hersko; Kelly L. McDow-Dunham

[57] ABSTRACT

A technique for in vitro testing of ocular and dermal irritants is disclosed. The process involves the topical application of liquid, solid granular or gel-like materials (e.g. cosmetics) to a cell culture and then evaluating the cytotoxicity of the material. Cell cultures of human skin without a stratum corneum and having a histologic similarity to the eye are used. Irritation is evaluated by measuring cell viability using MTT assay (based on the reduction of a tetrazolium dye by functional mitochondria), or release of LDH or $PGE_2$. A unique method of applying test materials which are not water soluble is described.

9 Claims, 2 Drawing Sheets

IN VITRO METHOD FOR EYE AND SKIN IRRITATION TESTING

This is a continuation of application Ser. No. 08/378,897, filed on Jan. 26, 1995, now abandoned, which is a continuation of application Ser. No. 08/115,901, filed on Sep. 1, 1993 now abandoned, which is a continuation of application Ser. No. 07/838,594 filed on Feb. 19, 1992, now abandoned.

TECHNICAL FIELD

A technique for in vitro testing of ocular and dermal irritants is disclosed. The process involves the topical application of liquid, solid, granular or gel-like materials (e.g. cosmetics) and aqueous incompatible materials to a cell culture and then evaluating the cytotoxicity of the material.

BACKGROUND OF THE INVENTION

Currently, potential eye and skin irritation of many chemicals, household cleaning products, cosmetics, paints and other materials are evaluated through direct application to animals or human subjects. A common way of measuring the irritancy and effect of material on the eye or skin is through the Draize test in which a material is applied directly to a rabbit's eye or skin and the irritation measured. (Draize, J. H., Woodward, G. and Calvery, H. O. (1944), "Methods for the Study of Irritation and Toxicity of Substances Applied Topically to the Skin and Mucous Membranes", *J. of Pharm. and Exp. Therapeutics,* 82; 377–390). A low volume test for eye irritation has been devised but this still requires living subjects.

Previously a skin keratinocyte Neutral Red assay method for in vitro assessment of skin Irritation was developed for testing chemical ingredients. (Osborne, R. and Perkins, M. A. (1990), "In Vitro Skin Irritation Testing with Human Skin Cell Cultures", *Toxic in Vitro* 5, 563–567, U.S. patent application Ser. No. 07/647,379, filed Jan. 28, 1991). These keratinocyte cell cultures are submerged in an aqueous buffered medium during the testing. Therefore any material which is added to the culture must also be soluble in the buffered medium used to grow this culture. Any test materials must be compatible with water and able to be diluted. Therefore, these systems are limited in their ability to predict the irritancy potential for aqueous incompatible materials, solid or gel-like product formulations, and acids or bases which would react with the buffer. Moreover, cultures which are submerged in a buffered medium cannot mimic the in vivo topical application methods in which neat materials are applied directly to the eye or skin surface.

Therefore, there is a need to provide a method of evaluating topically applied neat materials in vitro. A method in which materials could be placed directly onto the cell culture and the effect or irritation of the material studied over time is highly desirable. It is an object of the invention herein to provide a method for topical application of neat (undiluted) test materials as an alternative model for eye and skin irritancy testing. Skin cultures without a stratum corneum that have a histologic similarity to both eye and skin morphology are used. The cytotoxicity of test materials to the cells is determined by MTT assay. MTT assay for cell viability is based on the reduction of a tetrazolium dye by functional mitochondria. Other biochemical endpoints such as the release of the cytosolic enzyme lactate dehydrogenase (LDH), and the inflammatory mediator protaglandin $E_2$ ($PGE_2$), can be measured. These markers correlate with human skin irritation responses.

It is an object of this invention to provide an alternative method to eye and skin irritation testing in rabbits or other living models that is able to predict human irritancy potential of all types of formulations, including solid, granular and gel-like household cleaning products and cosmetics.

It is another object of this invention to provide novel topical application methods for problem test materials for example, gels, foams, pastes, granular materials, creams, solids, powders and acids or bases. It is a further object to provide a method which works for aqueous incompatible test materials.

SUMMARY OF THE INVENTION

A method for in vitro testing of ocular irritancy of chemicals and products is disclosed. The test materials can be liquid, solid or gel-like and do not have to be soluble in water. The method involves the following steps:

1) applying the test material directly on a sample holder, preferably a glass coverslip (diameter approx. 18 mm) having a thickness of approx. 0.25 mm and then placing the epithelial side of a skin culture onto the treated coverslip;

2) inverting the culture onto a filter holder placed inside a cell well containing assay medium;

3) incubating the culture for from 10 seconds to 60 minutes;

4) removing the sample holder from cell culture well and removing the culture mesh from sample holders or treatment coverslips;

5) gently wiping the culture to remove residual test material and washing the cell culture with phosphate buffered saline;

6) analyzing for cell viability using MTT.

The assay medium can be tested for LDH and $PGE_2$ release. A method for applying test materials to skin cultures used to measure skin irritancy is also disclosed. This method involves the following steps:

1) applying the test material directly on a sample holder, preferably a glass coverslip (diameter approx. 18 mm) having a thickness of approx. 0.25 mm and then placing the epithelial side of a skin culture onto the treated coverslip;

2) inverting the culture onto a filter holder placed inside a cell well containing assay medium;

3) incubating the culture for from 10 seconds to 60 minutes;

4) removing the sample holder from cell culture well and removing the culture mesh from sample holders or treatment coverslips;

5) gently wiping the culture to remove residual test material and washing the cell culture with phosphate buffered saline.

DETAILED DESCRIPTION OF THE INVENTION

Figure 1:
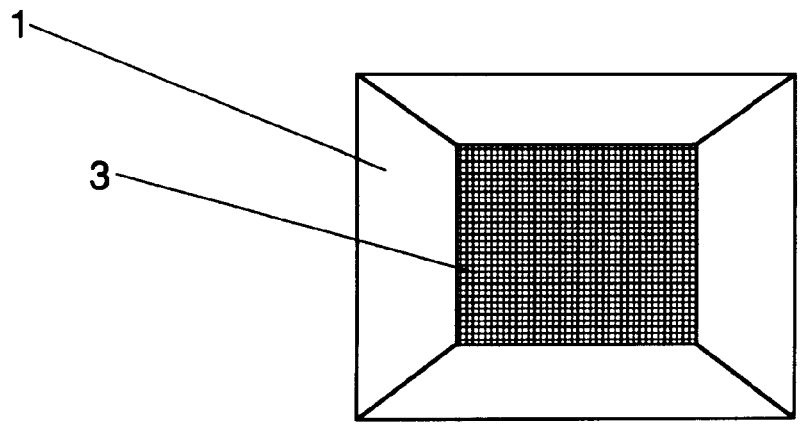
FIG. 1 is a top view of a dispenser used to apply dry granular materials. It comprises a hopper (1) to hold the powdered sample and a screen (3).

As used herein, the term "comprising" means various additional steps can be used in this process so long as they do not adversely affect the test results. Accordingly, the terms "consisting essentially of" and "consisting of" are embodied in the term comprising.

As used herein, "test material" means the composition which is being tested for ocular or skin irritancy. Test materials include acids and bases (e.g. sodium hydroxide, potassium hydroxide, hydrochloric or sulfuric acid), surfactants, detergents, bleaches, cosmetics, deodorants, shampoos, mascaras, nail polish, liquid and solid cleansers and any other suspected irritant.

The "effective time of treatment" is the amount of time needed to see a result. This will usually be from 10 seconds to 1 hour. The maximum results are usually evident at 30–40 minutes, but are dependent on the characteristics of individual test materials.

As used herein, "sample holder" or "cover slip" means a thin glass plate used to hold the test material. Non-permeable materials other than glass, e.g. metals or plastics could be used, but they are not preferred due to cost and relative availability. Preferred are circular coverslips (18 mm diameter) for microscope slides. The diameter should be slightly larger or approximate the size of the cell culture but can vary from 0.10 mm to about 0.20 mm. The plates are approx. 0.25 mm thick, but can vary from 0.20 mm to about 0.50 mm. Solids, gels and liquids are applied using a sample holder.

Solid materials can be applied directly to the cell culture if they are in the form of a granule or powder. These solids are generally ground to a particle size of less than 40 mesh size (420 microns).

The treated skin cell cultures are placed in a culture well containing assay medium. The cultures are placed on holders which are filters with ~3.0 $\mu$m pores in them to allow for passage of LDH and $PGE_2$ to the assay medium below and are referred to as transwells.

The method described herein can be used to test a variety of materials which come into contact with the eye or skin. These include surfactants (anionic, cationic, or nonionic), and products containing these surfactants, e.g. shampoos, detergents, fabric softeners, conditioners, dishwashing liquids, skin cleansers, cleaning agents and skin care items. Other materials and products that come into contact with the eye or skin can also be tested. These include permanent waving solutions, hair straighteners, hair dyes, cosmetics, moisturizers, colors and dyes used in cosmetics, sunscreens and tanning agents. These materials all have a potential to come into contact with human eyes and skin, and so need to be adequately tested for irritancy potential.

The following description of the assays and testing method can be applied to a number of products which contact the eyes or skin.

Cell Cultures: Two types of cell cultures are used. For eye irritation assessments, human skin cell co-cultures consisting of human neonatal foreskin fibroblasts and keratinocytes seeded onto an inert medical grade nylon mesh are used. These cultures (Skin$^2$ model) are available from Advanced Tissue Science, Inc. (ATS), formerly Marrow-Tech (10933 North Torrey Pines Road, LaJolla, Calif. 92037). Skin$^2$ cultures have a cellular organization that is similar to cornea, and so these cultures are appropriate for assessing potential cornea damage and irritation. The cell co-cultures if air interfaced can contain a stratum corneum layer which resembles skin. This layer has differentiated keratinocyte cells and is a human skin equivalent (HSE). For skin irritation assessments, a stratum corneum containing culture may be appropriate. A skin equivalent culture of this type is available from ATS. A similar culture grown in a collagen matrix on a filter is available from Organogenesis (83 Rogers Street, Cambridge, Mass. 02142). Clonetics (9620 Chesapeake Drive, San Diego, Calif. 92123) has human skin keratinocyte and dermal fibroblast monolayer cell culture models.

As used herein, "HuK/F" refers to these human skin neonatal foreskin keratinocyte and fibroblast co-cultures manufactured by ATS as the Skin$^2$ Model.

The HuK/F and HSE systems have advantages over other commercially available eye or skin toxicity testing systems in that they are morphologically similar to human eye and skin. One problem inherent in in vitro models is that cell cultures present physical problems regarding the solubility, stability and biophysical effects of the test compound in the aqueous culture medium in which the cells are grown and treated. Stratum corneum-containing HSE cultures allow application of test material to the surface of the cell layer in the same manner that materials come into contact with skin. For eye irritation assessments, the HuK/F model is preferred because it allows for direct contact of test substances with living epithelial cells, and therefore mimics corneal exposures.

One great advantage in skin irritation toxicology is the availability of human data for comparison with in vitro data. Unfortunately, these studies utilize a wide range of experimental protocols varying in exposure time, degree of occlusion, patch type, use of abrasion, application site, and duration of exposure and observation. The human skin irritation data is also based on a very subjective endpoint (i.e., visual skin grading for erythema and edema, 0–4 grades). Comparing the more quantitative in vitro data with the human data can be problematic. While eye irritation studies are also based on subjective assessments, more standardized protocols are used. Therefore, in vitro data for ocular irritation is more easily compared.

The development of a battery of objective quantitative biomarkers of skin irritation utilizing cytotoxicity (e.g. MTT assay) and irritancy endpoints (e.g. LDH & $PGE_2$) in HuK/F assay) and irritancy endpoints (e.g. LDH & $PGE_2$) in HuK/F co-cultures and HSE skin equivalents is based on the evaluation of cells and culture medium from skin cultures treated with irritants. (Osborne, R., and Perkins, M. A., "Evaluations of Human Skin Cell Cultures for In Vitro Skin Irritancy Testing from Alternative Methods in Toxicology", 8, A. M. Goldberg, Editor, pages 317–324 (1991).

MTT assay for cell viability (based on the reduction of a tetrazolium dye by functional mitochondria) is preferred to the neutral red assay (hereinafter referred to as, "NR") which is based on incorporation of NR dye into the lysosomes of viable cells. The preference is due to greater maximal incorporation of MTT, and a lower nonspecific binding of dye to nylon meshes for MTT versus NR.

In HuK/F cultures treated between 10 seconds and 1 hour, there are dose dependent changes in cell viability (MTT incorporation), cytotoxicity (lactate dehydrogenase (LDH) and prostaglandin $E_2$ ($PGE_2$) generation in response to the materials tested. There is a close correlation among the endpoints for responses to the test materials, and between the in vitro responses and ocular irritation responses to the test materials.

Process

A. Cells

For ocular irritation assessments, skin cultures comprising fibroblasts and keratinocyte layers but no stratum corneum layers are used. A preferred culture is ATS Skin$^2$ (Model ZK1200) human skin cell cultures. The cultures are cleaned of shipping agar with assay medium (DMEM-based with 2% fetal bovine serum-FBS), according to the methods described in the ATS standard procedures manual supplied with this model. Meshes are shipped epithelial side up so care must be taken to keep this side up in all mesh transfers. Each culture mesh is placed aseptically into 24 well plates with ATS assay medium (2 ml/mesh) on the day before (<24 hours) each study to remove excess FBS from the cultures. Cultures can be maintained in the ATS DMEM based growth medium which contains 10% FBS until ≦24 hours prior to the experiment at which time they will be transferred to assay medium. All cultures are maintained in a humidified environment at 37° C. and at 5% $CO_2$ throughout the experiment, except for short treatment periods of less than 5 minutes (that are performed with pre-equilibrated medium in the culture hood). Cultures are preferably used for experimentation within 2 days of arrival.

B. Test Material Preparation

Dry powders or granular test materials are generally ground with a mortar and pestle until they can easily go through a #40 copper sieve. These materials are pre-weighed in 8 dram glass vials, or similar dispensers. Solid materials (e.g. deodorant sticks, makeup concealers, lipsticks) that are not easily ground are pre-softened by creaming. A portion can be mixed directly in a weigh boat using a curved metal spatula or other implement. Then the test materials are placed in a 5 or 10 ml syringe affixed with a three-way stopcock attached to a second syringe. The sample will be pushed from one syringe to the other until the consistency can be readily pipeted with a positive displacement pipet.

For highly irritating materials (e.g. sodium hydroxide or strong acids or bases where irritation occurs within 1 minute of treatment) a range of dilutions is evaluated. Dilutions are made from the liquid "neat" material using appropriate volumes of deionized distilled water or other appropriate solvent. In the case of solids, which are not tested neat in-vivo, a weighed amount is prepared in deionized distilled water, or other appropriate solvent, and then diluted to prepare lower concentrations. All treatments are vortexed at high speed and visually inspected for homogeneity.

In order to determine the optimal time for treatment of the cultures, time-course experiments examining the responses of HuK/F cultures to various materials need to be conducted. Significant responses were seen at 30 minutes after treatment in most cases.

For MTT endpoints there was good agreement with eye irritation responses to the test materials.

C. Treatment Application and Removal Methods

One day prior L≧24 hours) to the experiment, all meshes are placed in 2 ml/well of assay medium. The transwell filter plate inserts are pre-wetted by incubating the number needed for each study in 1.5 ml of assay medium at 37° C. and 5% $CO_2$. On the day of study this medium is aspirated and replaced with exactly 1.5 ml of fresh assay medium, pre-warmed to 37° C.

Generally, 25 µl of each treatment material is pipeted, using a Gilson positive displacement pipet, onto the sample holder, e.g. a round coverslip. These are standard microscope cover slips. All treatment groups contain at least 2 culture meshes. Thick or viscous treatments are spread out on the coverslip using the pipet tip so that the material approximates the area of the culture mesh. This can be accomplished by placing a blank mesh (ATS Part #ZB1000) under the coverslip to be used as a template. If material cannot be pipeted then 25 mg of test material is weighed directly onto a tared glass coverslip and spread to the mesh size (1 cm²) using a pipet tip. The treatment mesh is then removed from the assay medium and placed epithelial side down onto the treatment material. The treated mesh with cover slip is then inverted and placed fibroblast side down onto the transwell filter. All treatment times ≧5 minutes will be placed in a 37° C., 5% $CO_2$ incubator for the treatment period.

In the case of dry powders/granulars, 25 mg of these materials are delivered directly onto the cell mesh (placed epidermis side up in the transwell) via a special delivery hopper (see FIG. 1). A cover slip or sample holder is placed on the top of the treatment mesh. Assay medium alone, applied to the coverslip with a culture mesh applied as above, will act as a time matched control.

Test Material Removal

At the end of the treatment time, meshes and transwells are removed from the 6 well plate and placed on absorbant paper. The mesh is immediately removed from the coverslip and cleaned of treatment materials using PBS gently squeezed from a wash bottle. In addition to rinsing with PBS, the mesh is gently scraped along the smooth edge of the treatment transwell or a glass beaker to remove any remaining test material. The mesh will be repeatedly rinsed and scraped until it appears clean or with the least amount of test material adhering on visual inspection (surface appears dull). For surfactant containing test materials (e.g. shampoos, soaps, detergents) extra care must be taken to remove test material with copious amounts of PBS (50–100 ml). The cleaned mesh is transferred to a 24 well culture plate containing 1 ml of (ATS) assay medium per well. Meshes are collected into this assay medium until all treatments are completed.

Sample Collection and Analysis

After the treatment period the medium samples are collected (1.5/ml per well) and split into two 0.75 ml aliquots. One 0.75 ml aliquot is analyzed for lactate dehydrogenase, using Boehringer-Mannheim biochemicals automated on an Boehringer autoanalyzer. The second 0.75 ml sample is collected in a polypropylene tube and purged with nitrogen, immediately placed in liquid nitrogen vapor and stored frozen at −70° C. These samples are subsequently analyzed for Prostaglandin $E_2$ by radioimmunoassay (Advanced Magnetics kit #6001).

Cell Viability Assay

The MTT assay measures the reduction of a tetrazolium dye by electron transport in mitochondria of viable cells, and subsequent intracellular trapping of the formazan product.

The MTT Assay was adapted from a method described in Mossmann, T., Rapid Colorimetric Assay for Cellular Growth and Survival: Application to proliferation and cytotoxicity assays, *Journal of Immunological Methods:* 65:55–63, (1983). It is a measure of cell viability, and is performed on all treatment meshes immediately following completion of an experiment. The MTT assay quantitates the reduction and subsequent trapping of a yellow tetrazolium dye which is reduced by the electron transport chain of functional mitochondria to a purple formazan dye. Briefly, MTT (3 -[4,5-Dimethylthiazol-2-yl]-2,5-diphenyltetrazolium bromide; Sigma Catalog #M-2128) powder is diluted in cell culture medium (0.5 mg/ml) and pre-warmed to 37° C. before use. One ml of this dye solution is aliquoted onto each mesh, and the meshes are then incubated 3 hours at 37° C. and 5% $CO_2$ on a rotator at 100–200 rpm. After incubation, the MTT is aspirated, and 2 ml of pure isopropanol is used to extract the reduced dye for two hours at room temperature on the rotator. The meshes are removed from the culture well and extraction solvent mixed by stirring before aliquoting for absorbance readings. The absorbance of each extract is read at 540 nm on a Biotek EL-312 (96 well) spectrophotometer.

ANALYTICAL METHODS

MTT Assay Protocol For 24 Well Full Thickness Skin Cultures on Mesh

1. Place one untreated, blank mesh (no cells) into one or more wells to determine the background non-specific binding (NSB) of MTT to mesh and to act as absolute blank.

2. Prepare a solution of 0.5 mg/ml MTT (Sigma Chemical Co. Catalog #M-2128) in assay medium. Centrifuge MTT/medium for 5 minutes at 3000 RPM to pellet undissolved crystals, then prewarm MTT in a 37° C. waterbath.

3. Remove medium.

4. Add 1 ml/well MTT/medium solution. Incubate cultures at 37° C., 5% carbon dioxide for 3 hours on a rotator set at 100–200 RPM.

5. Remove MTT/medium and wash each mesh on a rotator at 100–200 rpm with 1 ml Dulbecco's phosphate buffered saline with calcium and magnesium (PBS) for 2 mins.

6. Remove PBS wash and add 2 ml isopropanol/well at room temperature 2 hours with rotation. This will extract the formazan from mitochondria of cells into the supernatant. (Note: the amount of MTT taken up by a cell culture and subsequently released by solvent extraction is proportional to the number of viable cells within the culture). Remove meshes from test well and mix.

7. Transfer 200 microliter aliquots of the blue spent solvent from each well to a 96 well microtiter plate and read absorbance at 540 nm. The wells containing the NSB meshes should be subtracted from the test well absorbances before performing calculations below.

T-50 Calculations. The endpoint of the MTT assays used for reporting the toxicity of test agents is the time which results in a 50% decrease in MTT dye uptake (i.e., T-50) when compared to untreated control values. Calculations were performed as follows:

1) Calculate the mean OD 540 (optical density at 540 nm) of the untreated control wells. Note: When assays were performed on culture mesh, a non-specific binding (NSB) control was evaluated and this value subtracted from each control and treatment absorbance.

2) Calculate the mean OD 540 of the wells for each time point of test agent.

3) Calculate the % of UNTREATED CONTROL for each mean OD 540:

$$\frac{\text{Mean OD 540 of test agent treated mesh}}{\text{Mean OD 540 of untreated control}} \times 100 = \% \text{ of untreated control}$$

Figure 2:
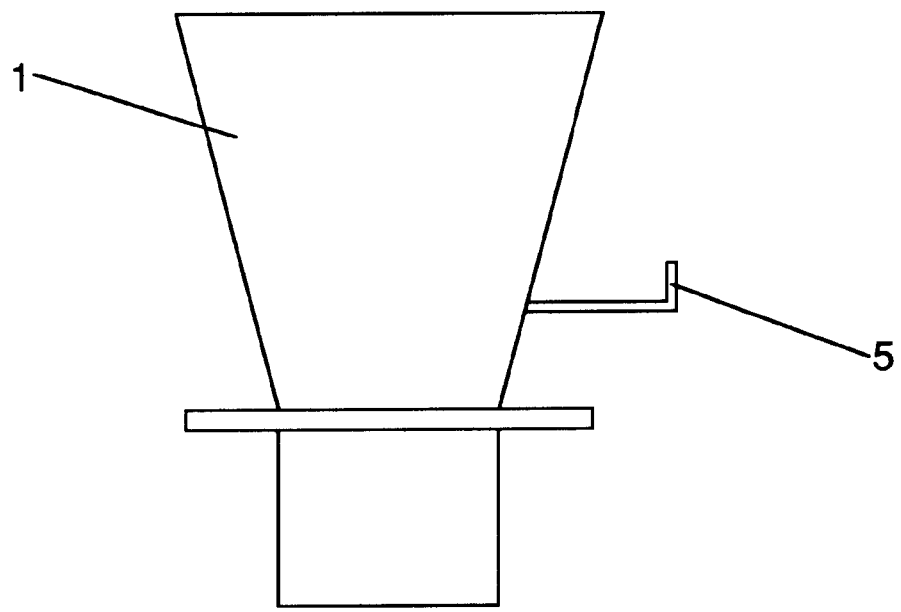
FIG. 2 is a side view of the dispenser. The trap door below the screen is shown as (5). The dispenser is about 2 in. (5 cm) square at the top.
Figure 3:
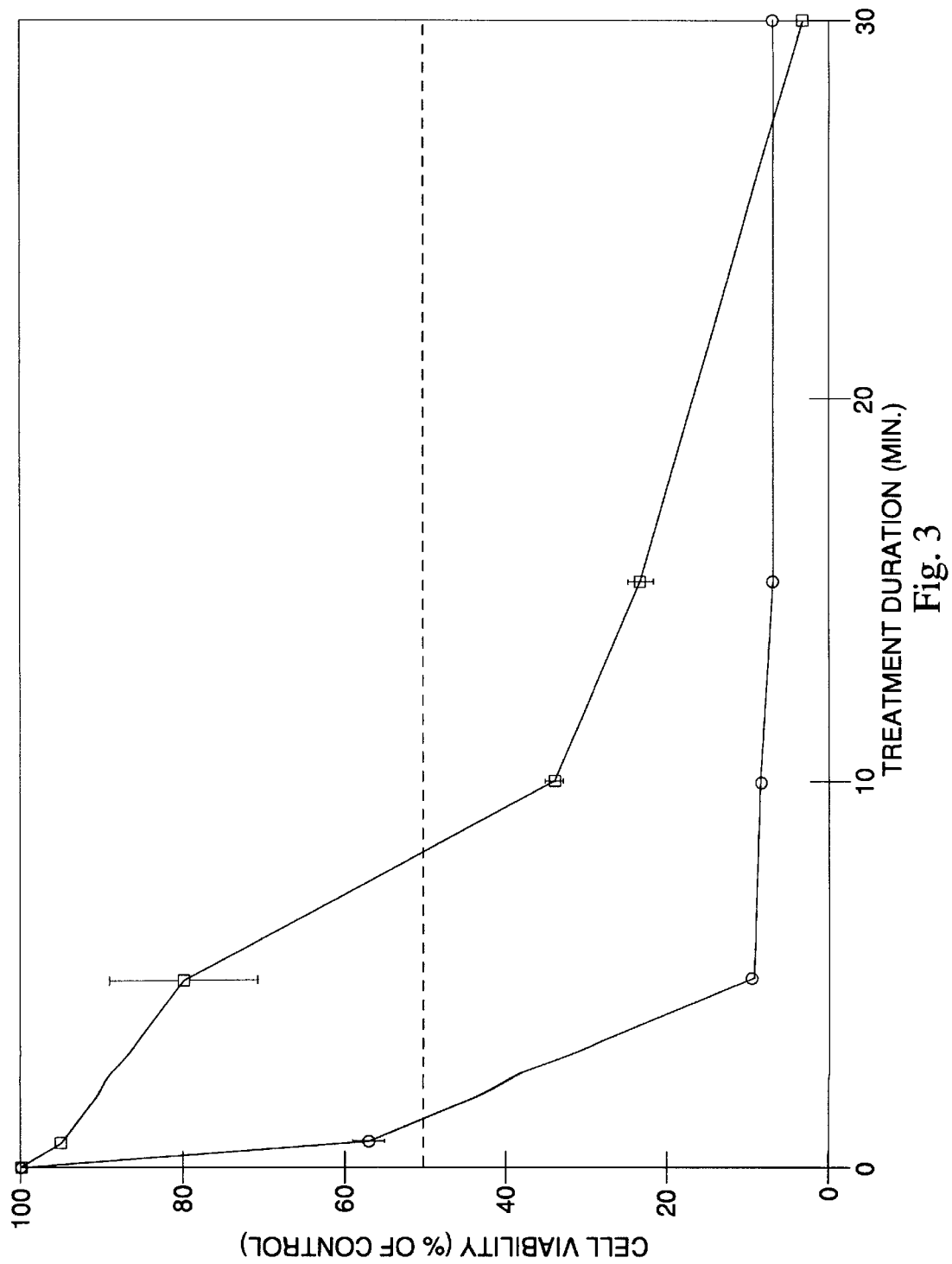
FIG. 3 is a typical curve used to measure to obtain T-50 values.

On a semi-log graph, the % of Untreated Control was plotted on the y axis and the response time on the x axis to establish a time response curve for each test agent. A calculation using a similar triangle method incorporated into a statistical program was performed for each test agent dose response curve to determine the T-50 treatment time. The T-50 represents the time in which cell viability (Y-axis) was decreased by 50% of the untreated control value. FIG. 2 is a representative curve.

The MTT assay measures the number of cells which are viable. The cells can be treated at different exposure times to get a range of responses, from little or no effect to killing of all the cells. The T-50s for test agents within a chemical class may be used to rank order their relative toxicities.

Results

Several substances were tested by the method described above and the T-50 values compared to historical data using the low volume eye test (LVET). These results are reported in Table I. The correlation of the data enables one to predict the irritancy of the material. A T-50 of less than 1 minute is considered strongly irritating, from 1 to 10 minutes is mild to moderate, and above 10 minutes is considered slight to inocuous in irritation potential.

TABLE I

|  | T-50 (min.) | LVET |
|---|---|---|
| Strong Test Substances |  |  |
| 10% sodium hydroxide | 0.09 | 90 |
| dish detergent | 0.29 | 30 |

TABLE I-continued

|  | T-50 (min.) | LVET |
|---|---|---|
| calcium hydroxide (powder) | 0.28 | 45 |
| Mild to Moderate |  |  |
| laundry detergent 2 | 8.0 | 5.5 |
| skin care cream 2 | 2.5 | 13.0 |
| liquid cologne | 6.5 | 2.2 |
| Inocuous to Slight |  |  |
| skin care cream 3 | 30.0 | 0.7 |
| liquid fabric softener | 30.0 | 5.3 |
| dish care granular | 16.1 | 4.0 |
| toothpaste | 12.3 | 0.7 |

In the low volume eye test the test material was placed directly on the cornea in 3 animals. The average maximum score for irritation is reported. Corneal injury is scored 80 out of a possible 110 points. The remaining points are from evaluation of the iris, redness, swelling and discharge from the conjunctiva.

What is claimed is:

1. A method for testing in vitro epithelial and ocular irritancy of a test material comprising:

A. selecting the test material from the group consisting of a neat liquid, a water-insoluble solid, and a water-insoluble gel-like material;

B. applying the test material directly to at least one side of a planar non-permeable sample holder;

C. contacting the side of the sample holder with the test material applied thereto directly to a cell co-culture whereby the test material is contacted to the cell co-culture for a time period from 10 seconds to 60 minutes; and D. measuring irritancy of the test material by using one or more assays selected from the group consisting of a 3-(4,5-dimethylthiazol-2-yl)-2,5-diphenyltetrazolium bromide assay, a LDH release assay, and a $PGE_2$ release assay.

2. The method according to claim 1 wherein the test material is insoluble in water.

3. The method according to claim 2 wherein the non-permeable sample holder is plastic, metal or glass.

4. The method according to claim 3 wherein the non-permeable sample holder is glass.

5. The method according to claim 1 wherein the cells comprising the co-culture have a stratum corneum layer.

6. The method according to claim 1 wherein the test material is a water-insoluble material selected from the group consisting of surfactants, cosmetics, sunscreens, hair dyes, permanent waving solutions, hair straighteners, colors and dyes used in cosmetics, tanning agents, an moisturizers.

7. The method according to claim 1 wherein the co-culture is comprised of human keratinocyte and fibroblast cells.

8. The method according to claim 7 wherein the cells comprising the co-culture are derived from human neonatal foreskin.

9. The method according to claim 8 wherein the cells have a stratum corneum layer.

* * * * *